Jan. 29, 1952 P. ECKE Plant Pat. 1,068
POINSETTIA PLANT
Filed July 7, 1950
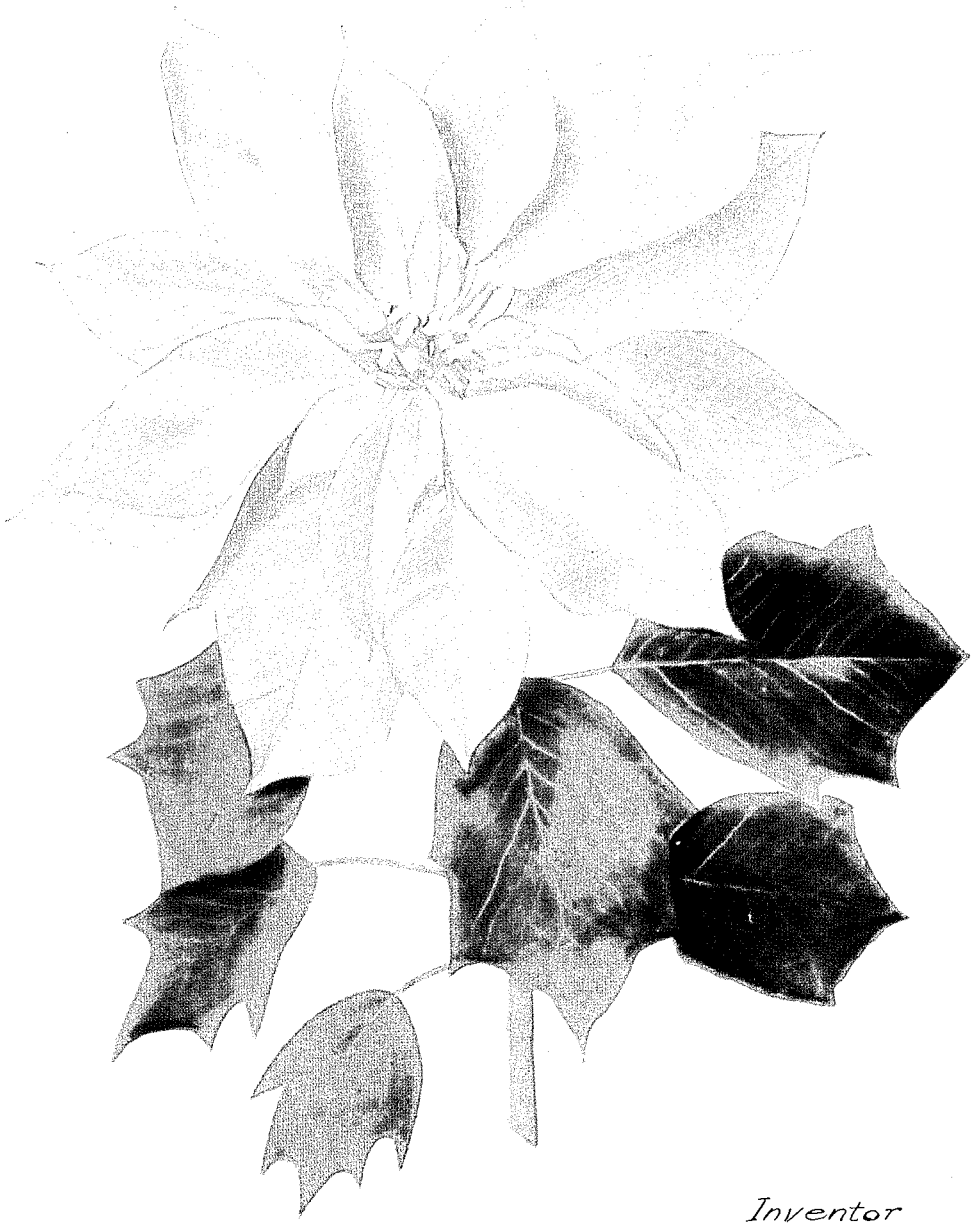
Inventor
Paul Ecke
By M. S. Graham
Attorney Patented Jan. 29, 1952

Plant Pat. 1,068

UNITED STATES PATENT OFFICE 1,068

POINSETTIA PLANT

Paul Ecke, Encinitas, Calif.

Application July 7, 1950, Serial No. 172,477

1 Claim. (Cl. 47—60)

The present discovery to a new and distinct variety of poinsettia plant (*Euphorbia pulcherrima*), originating as a sport.

Broadly, this new variety of poinsettia plant is distinguishable from the parent plant as well as from other known varieties, mainly in the shape, color and character of the bracts and foliage leaves. More specifically, it is also distinguishable from other known varieties by the arrangement of the individual character of the bracts which are relatively long, wide, ovate-acuminate and overlapping in a rosette cluster, a majority of which are mounted on comparatively short petioles, so that the bract involucre is substantially closed at its center around the inflorescence.

The accompanying illustration, forming a part of this application, graphically shows in color the subject in its full maturity or optimum, the illustration being a face view of the subject, shown in its normal condition, with its characteristics which differentiate this new variety.

The colors referred to herein correspond approximately with those shown in "Horticultural Color Chart" issued by the British Color Council in collaboration with the Horticultural Society, and identified by the color name and plate of said color standard by recapitulation in tabular form herein.

The following is a detailed description of this new variety.

*Parentage*

This new variety was originated and discovered by me in a cultivated area of a glasshouse or greenhouse at my experimental and growing gardens at Encinitas, San Diego County, California, and originated as a cultivated sport of poinsettia plant of the variety commonly known as Indianapolis Red poinsettia plant, not patented, but known in the trade by that name for many years.

The new variety has been asexually reproduced in my greenhouse or glasshouse by cuttings, and it has remained true to type and the herein described characteristics through the propagation of several thousand plants over a period of more than 3 years and has shown its qualities and characteristics to be permanently fixed. In asexually reproducing this new variety I have found it satisfactory and efficient to cut pieces of stalk of soft wood substantially six inches in length in the months of June, July and August, and embed one end of the cuttings in beds of sand in my glasshouse. After three or four weeks the cuttings are well rooted and may be transferred to individual pots.

*Structure*

The peduncles which branch from the main trunk are spinach green and are long, stiff and very strong. They are comparatively small in cross section. Their average length is four feet with several small pedicels at the top end usually growing as knob-like spurs, each of which bears a few sub-acaulescent flowers. From the base of the knob-like spurs also grows an involucre of bracts.

*Foliage leaves*

The foliage leaves are arranged around the peduncle and are usually in groups of three, the petioles of which radiate from the peduncle in relatively close longitudinal proximity, and the next adjacent group of three is longitudinally spaced along the peduncle a greater distance than the individual petioles of the three-leaf groups. The foliage leaves are of a modified oak-leaf type, generally ovate at the base portion and scalloped at the outer end portion, and have reticulate venation. The color of the foliage leaves is spinach green, and the petioles thereof are blood red.

*Bracts*

The bracts, in planar contour, are elongated and prolately ovate-acuminate. At the optimum of their maturity the bracts and their petioles are blood red in color, and maintain a uniformity of color in a wider differential range of temperature than known varieties of poinsettias.

The bracts are further characterized by a numerically greater number of individual bracts than known varieties of poinsettia, and the predominating majority of individual bracts are of greater axial length and greater transverse width and greater individual planar area than known varieties. Further, the petioles of the predominating majority of individual bracts are uncommonly short, which, together with the axial length and width of the bracts forms a rosette of the bracts involucre almost closed at its center around the inflorescence and with edges of individual bracts overlapping.

*Inflorescence*

A node is formed on the upper end of each peduncle, each of which usually presents three short and comparatively large heavy stem-like spurs which protrude upwardly and expansively apart, each spur providing the base for a plurality of flower cyathiums having short sub-acaulescent stems. Each cyathium produces a single pistillate flower surrounded by several chrome yellow staminate flowers. The cyathium, prior to maturity, is substantially white, and at maturity is of a scheeles green color. The pistillate flower pushes upward from the base of the cyathium and produces spread stigma which are of blood red color, the pistillate flower continuing to mature into a seed pod.

*Dimensions*

The total height of the plan at maturity, including main trunk and peduncles, is approximately eight feed, and the greatest lateral dimension is approximately four to five feet.

*Habits of growth*

This new variety is vigorous but slow in growth, easily cultivated, if properly handled, and persistent and perennial in growth. Foliage, bracts and inflorescence occur annually maturing in Southern California from November to December, the optimum elsewhere being modified by climate and growing conditions.

*Immunity*

The entire plant seems to be immune or highly resistant to disease and all other obnoxious and detrimental influences.

*Variations*

Different plants of this new variety have an unusual similarity of adherence to characteristics and type as herein described; however, in comparison with the same grown in various localities, in different soils, and at various times of the year, in different temperatures or in different greenhouses or in the open, and even by different persons, there may be slight variations of minor detail.

*Propagation*

Propagation is by cuttings taken at any time from May until September, and the plant will mature to optimum from November to December, retaining bracts and foliage for substantially two months, after which the plant will remain dormant for three months.

*Color tabulations*

The color designations according to the color plates of said "Horticultural Color Chart" are recapitulated in tabular form as follows:

| Element | Color | Sheet | Plate |
|---|---|---|---|
| Peduncles | Spinach Green | 187 | °960/3 |
| Petioles of Foliage Leaves | Blood Red | 166 | 820 |
| Foliage Leaves | Spinach Green | 187 | °960 |
| Bracts | Blood Red | 166 | 820/1 |
| Inflorescence: | | | |
| Cyanthium (at maturity) | Scheeles Green | 175 | 860/3 |
| Staminate flowers | Chrome Yellow | 144 | 605 |
| Pistil | Blood Red | 166 | 820 |

Having described and illustrated my new variety of Poinsettia Plant, I claim:

A new and distinct variety of poinsettia plant substantially as illustrated and described, characterized by a central inflorescence and a large number of bracts of rich blood red color and in which the individual bracts are prolately ovate-accuminate and comparatively wide throughout the major portion of their axial length, and in which the petioles of individual bracts are comparatively short whereby a bract involucre is provided in which the bases of the bracts closely surround the inflorescence and the side edges of individual bracts overlap the edge of the next adjacent bracts.

PAUL ECKE.

No references cited.